United States Patent
Bathina et al.

(10) Patent No.: US 10,898,266 B2
(45) Date of Patent: Jan. 26, 2021

(54) METHOD AND SYSTEM FOR PERSONALIZING A VESSEL STENT

(71) Applicants: Yogesh Bathina, Bangalore (IN); Antony Louis Piriyakumar Douglas, Bangalore (IN); Rajendra Prasad Jadiyappa, Karnataka (IN); Amit Kale, Karnataka (IN)

(72) Inventors: Yogesh Bathina, Bangalore (IN); Antony Louis Piriyakumar Douglas, Bangalore (IN); Rajendra Prasad Jadiyappa, Karnataka (IN); Amit Kale, Karnataka (IN)

(73) Assignee: Siemens Healthcare GmbH, Erlangen (DE)

( * ) Notice: Subject to any disclaimer, the term of this patent is extended or adjusted under 35 U.S.C. 154(b) by 194 days.

(21) Appl. No.: 15/674,296

(22) Filed: Aug. 10, 2017

(65) Prior Publication Data
US 2017/0367765 A1    Dec. 28, 2017

Related U.S. Application Data

(63) Continuation-in-part of application No. PCT/IB2015/000168, filed on Feb. 17, 2015.

(51) Int. Cl.
*A61B 34/10* (2016.01)
*G05B 19/40* (2006.01)
(Continued)

(52) U.S. Cl.
CPC ............... *A61B 34/10* (2016.02); *A61F 2/82* (2013.01); *B33Y 50/00* (2014.12);
(Continued)

(58) Field of Classification Search
CPC ... A61B 34/10; A61B 6/469; A61B 2034/108; A61B 5/004; A61B 6/032; A61B 6/037;
(Continued)

(56) References Cited

U.S. PATENT DOCUMENTS

| | | | | |
|---|---|---|---|---|
| 6,896,697 B1 * | 5/2005 | Yip | ......................... | A61F 2/915 623/1.15 |
| 7,018,403 B1 * | 3/2006 | Pienknagura | ............. | A61F 2/91 623/1.15 |

(Continued)

FOREIGN PATENT DOCUMENTS

| | | |
|---|---|---|
| CN | 1504931 A | 6/2004 |
| CN | 101578631 A | 11/2009 |

(Continued)

OTHER PUBLICATIONS

PCT International Search Report for corresponding PCT/IB2015/000168, dated Feb. 17, 2015.
(Continued)

*Primary Examiner* — Mohammad Ali
*Assistant Examiner* — Kelvin Booker
(74) *Attorney, Agent, or Firm* — Lempia Summerfield Katz LLC (57) ABSTRACT

For personalizing a vessel stent, images associated with a subject generated by various imaging modalities are aggregated. The images are then processed for identifying Regions of Interest (ROIs) and various parameters associated with the ROIs. Further, a model and a composition of the vessel stent to be administered to the subject to alleviate the condition in the vessel are computed. Thereafter, the model is verified for compatibility using information derived from patient stratification parameters. Upon successful verification of the model, a format of the model is generated that (Continued)

US 10,898,266 B2

Page 2 can be used directly for fabricating the vessel stent using additive manufacturing processes known in the art.

16 Claims, 8 Drawing Sheets

(51) Int. Cl.
| | | |
|---|---|---|
| *A61F 2/82* | (2013.01) | |
| *B33Y 50/00* | (2015.01) | |
| *G05B 19/4099* | (2006.01) | |
| *A61B 5/00* | (2006.01) | |
| *A61B 6/03* | (2006.01) | |
| *A61B 6/00* | (2006.01) | |
| *A61B 8/00* | (2006.01) | |

(52) U.S. Cl.
CPC .......... *G05B 19/4099* (2013.01); *A61B 5/004* (2013.01); *A61B 6/032* (2013.01); *A61B 6/037* (2013.01); *A61B 6/469* (2013.01); *A61B 6/504* (2013.01); *A61B 8/469* (2013.01); *A61B 2034/108* (2016.02); *A61B 2576/02* (2013.01); *A61F 2210/0071* (2013.01); *A61F 2240/002* (2013.01); *A61F 2240/004* (2013.01); *A61F 2250/0039* (2013.01); *G05B 2219/35134* (2013.01); *G05B 2219/49007* (2013.01)

(58) Field of Classification Search
CPC ..... A61B 6/504; A61B 8/469; A61B 2576/02; G05B 19/4099; G05B 2219/49007; G05B 2219/35134; B33Y 50/00; A61F 2/82; A61F 2240/004; A61F 2210/0071; A61F 2250/0039; A61F 2240/002
See application file for complete search history.

(56) References Cited

U.S. PATENT DOCUMENTS

| | | | | |
|---|---|---|---|---|
| 7,331,987 B1* | 2/2008 | Cox | ............... | A61F 2/91 623/1.16 |
| 7,572,286 B1* | 8/2009 | Chen | ............... | A61F 2/91 623/1.13 |
| 7,731,744 B1* | 6/2010 | Cox | ............... | A61F 2/915 623/1.14 |
| 9,042,613 B2* | 5/2015 | Spilker | ............... | G06K 9/46 382/128 |
| 9,114,032 B1* | 8/2015 | Pulugurtha | ............... | C23F 1/02 |
| 10,183,442 B1* | 1/2019 | Miller | ............... | B29C 64/118 |
| 2001/0053931 A1* | 12/2001 | Hess | ............... | A61F 2/07 623/1.15 |
| 2002/0068968 A1* | 6/2002 | Hupp | ............... | A61F 2/856 623/1.15 |
| 2002/0188345 A1* | 12/2002 | Pacetti | ............... | A61F 2/86 623/1.15 |
| 2003/0197734 A1* | 10/2003 | Binkert | ............... | G06Q 10/10 715/771 |
| 2003/0200120 A1* | 10/2003 | Binkert | ............... | G06F 19/3481 705/3 |
| 2004/0230293 A1* | 11/2004 | Yip | ............... | A61F 2/915 623/1.16 |
| 2007/0168066 A1 | 7/2007 | Grishaber et al. | | |
| 2007/0265698 A1* | 11/2007 | Pienknagura | ............... | A61F 2/91 623/1.16 |
| 2007/0293756 A1* | 12/2007 | Jung | ............... | G06Q 10/06 600/427 |
| 2007/0293936 A1* | 12/2007 | Dobak, III | ............... | A61F 2/07 623/1.13 |
| 2007/0294280 A1* | 12/2007 | Jung | ............... | A61B 1/00082 |
| 2008/0107315 A1 | 5/2008 | Kimmel et al. | | |
| 2008/0188924 A1* | 8/2008 | Prabhu | ............... | A61F 2/82 623/1.16 |
| 2008/0201007 A1* | 8/2008 | Boyden | ............... | G06T 17/00 700/119 |
| 2008/0234802 A1* | 9/2008 | Dancu | ............... | G09B 23/28 623/1.41 |
| 2008/0234806 A1* | 9/2008 | Dancu | ............... | G09B 23/28 623/1.41 |
| 2009/0007923 A1* | 1/2009 | Dancu | ............... | G09B 23/28 128/898 |
| 2009/0043373 A1* | 2/2009 | Arnault De La Menardiere | ........ | A61F 2/07 623/1.15 |
| 2009/0270974 A1* | 10/2009 | Berez | ............... | A61F 2/844 623/1.17 |
| 2009/0304245 A1 | 12/2009 | Egger et al. | | |
| 2010/0027862 A1* | 2/2010 | Kale | ............... | G06K 9/4609 382/131 |
| 2010/0228337 A1* | 9/2010 | Milisav | ............... | A61F 2/91 623/1.16 |
| 2011/0016690 A1* | 1/2011 | Narainasamy | ...... | A61F 2/30942 29/428 |
| 2012/0060969 A1* | 3/2012 | Pacetti | ............... | A61F 2/91 141/2 |
| 2012/0134564 A1 | 5/2012 | Zheng et al. | | |
| 2012/0330557 A1 | 12/2012 | Zhang et al. | | |
| 2013/0018665 A1* | 1/2013 | Jung | ............... | G06Q 10/08 705/2 |
| 2013/0178928 A1* | 7/2013 | Vyas | ............... | A61F 2/915 623/1.16 |
| 2014/0107764 A1* | 4/2014 | Bressloff | ............... | A61F 2/915 623/1.16 |
| 2015/0238333 A1* | 8/2015 | Berez | ............... | A61F 2/852 623/1.15 |
| 2015/0374243 A1* | 12/2015 | Itu | ............... | G06F 17/10 703/2 |
| 2016/0022371 A1* | 1/2016 | Sauer | ............... | G06F 19/321 600/407 |
| 2016/0022961 A1* | 1/2016 | Rosenman | ........ | A61M 25/0147 604/95.04 |
| 2017/0057169 A1* | 3/2017 | Grbic | ............... | B29C 64/386 |
| 2019/0365472 A1* | 12/2019 | Connor | ............ | A61B 17/12163 |

FOREIGN PATENT DOCUMENTS

| | | |
|---|---|---|
| CN | 102365061 A | 2/2012 |
| CN | 103854028 A | 6/2014 |
| CN | 103860294 A | 6/2014 |
| WO | WO2010120990 A1 | 10/2010 |
| WO | WO2012087434 A3 | 4/2014 |

OTHER PUBLICATIONS

Chinese Office Action for Chinese Application No. 201580076384.8 dated May 31, 2019.

* cited by examiner

METHOD AND SYSTEM FOR PERSONALIZING A VESSEL STENT

RELATED CASES

The present patent document is a continuation-in-part of PCT Application Serial Number PCT/IB2015/000168, filed Feb. 17, 2015, designating the United States, which is hereby incorporated by reference.

FIELD OF INVENTION

The present embodiments relate to a method and system for customizing a vessel stent for a subject. More particularly, the method and system relates to customizing the structure of the vessel stent based on one or more parameters associated with the subject.

BACKGROUND

Cardiovascular diseases (CVDs) have become the prime cause of death around the world. More people die of CVDs than any other cause. According to a report published by World Health Organization, an estimated 17.3 million people die every year due to CVDs. One of the common ailments in CVDs is the deposition of plaque in cardiovascular arteries. The plaque deposition can block the blood flow in the heart thereby resulting in myocardial ischemia or myocardial infarction.

One of the most common remedies for CVDs is deploying stents into the arteries where a significant plaque deposit is found. Currently, there are a number of prefabricated stents available in different sizes and shapes which can be inserted in the arteries based on an assessment by a doctor. However, the prefabricated stents cannot be personalized according to the nature of the plaque deposit in the affected vessel of the subject. Recently with the advancement of the additive manufacturing there is scope for manufacturing personalized stents. Therefore, there is a need for generating personalized vessel stents based on the nature of the plaque deposit in the cardiovascular arteries.

Accordingly, it is an object to provide a method and system for fabricating personalized vessel stents by considering various parameters associated with the subject and the nature of the plaque deposit in the vessel. The object is achieved by providing a method for customizing a vessel stent for a subject.

SUMMARY

In an aspect, the method includes a step of aggregating, by a processor, one or more images generated by one or more imaging modalities. The imaging modalities may include various diagnostic imaging modalities such as MRI scanning device, a PET scanning device, CT scanning device, Ultrasound scanning and the like. The imaging modalities may be located in different places and are connected through a network. The method further includes processing the said one or more images to obtain one or more regions of interest and one or more physiological parameters associated with one or more region of interest (ROI). The images aggregated may be processed to identify one or more regions of interest (ROI). Upon detecting the ROIs, one or more parameters such as the composition, length, structure and the calcification are determined based on the processing of the images. The method includes a step of generating a model of the personalized vessel stent based on the one or more parameters associated with the region of interest and one or more of the physiological parameters associated with the subject. The physiological parameters of the subject such as age, weight, gender, height and vital statistics are used to model the vessel stent.

The method further includes determining one or more materials for fabricating the personalized vessel stent based on the one or more parameters associated with the region of interest. In this step, the exact position and the nature of calcification of the plaque deposit are analyzed and the composition of the vessel stent is determined based on the analyses. The method includes a step of generating a format of the model of the personalized vessel stent for fabrication. The format may be communicated to an additive manufacturing device for fabricating the vessel stent.

In another aspect, the model of the personalized vessel stent is verified based on the one or more physiological parameters associated with the one or more ROI and one or more patient stratification parameters. The parameters associated with the one or more ROI includes a length, a thickness, a composition, a level of calcification and a distribution of a plaque deposition at the stenosed region In yet another aspect, patient stratification parameters are determined based on physical and physiological parameters of the subject. The patient stratification parameters may be a database of parameters based on the features such as race, ethnicity, age and sex. For example, the diameter of the arteries can be determined based on the aforesaid features, which can be used to test the personalized vessel stent.

In yet another aspect, the one or more ROIs include a stenosed region in a vessel. The stenosed region may include a plaque deposition. The stenosed regions in the vessel may include fatty deposits and calcified regions of varying thickness and length.

In still yet another aspect, the one or more materials for fabricating the personalized vessel stent are determined based on the parameters associated with the region of interest. The personalized vessel stent may be composed of a plurality of materials based on the parameters associated with the ROI. For example, if there is a protruding calcification in the stenosed region, the composition of the vessel stent may be modified to reduce the pressure exerted by the vessel stent over the calcified region.

In a further aspect, the one or more materials used in the fabrication of personalized vessel stent are selected from a group of metallic alloy, polyurethane and polyethylene. The materials may be chosen based on the parameters associated with plaque deposition at the ROIs.

In a further aspect, the fabrication of the personalized vessel stent is performed by an additive manufacturing process. The additive manufacturing processes may include selective laser sintering (SLS), fused deposition modelling (FDM), selective laser melting (SLM) and the like.

In order to fulfil the objective, a device for customizing a vessel stent for a subject is disclosed. The device includes a diagnostic imaging modality, wherein the imaging modality is capable of receiving and processing images from other imaging modalities. A processor and a memory coupled with the processor, wherein the memory includes processor executable instructions configured for personalizing the vessel stent. The memory includes a vessel stent personalization module. The vessel stent personalization module further includes an image registration module, an image processing module, a model generation module, composition determination module and a 3D print enabling module. The vessel stent personalization module and the associated modules are configured to perform appropriate functions as explained in the aforementioned method steps. For example, the image registration module is configured for processing the one or more images obtained from a plurality of imaging modalities. The image processing module is configured for determining one or more regions of interest and one or more parameters associated with one or more regions of interest (ROI).

In an aspect, the memory includes a verification module configured to verify the model of the personalized vessel stent based on the one or more parameters associated with the one or more ROI and one or more patient stratification parameters.

Additionally, the device is communicatively coupled with a 3D printer to fabricate the personalized vessel stent. The 3D print enabling module generates a format of the model of the personalized vessel stent which is used by the 3D printer to fabricate the vessel stent.

In order to fulfil the objective, a system for personalizing a vessel stent for a subject is disclosed. The system includes one or more diagnostic imaging modalities. The system also includes a processing unit, including a processor associated with the diagnostic imaging modality and memory associated with the processor comprising executable instructions configured for performing the method steps as explained earlier. Further, the system includes an additive manufacturing device, configured to fabricate the personalized vessel stent using the format of the model. Further, the system is configured to verify the model of the vessel stent using parameters based on patient stratification parameters obtained from the physical and physiological parameters of the subject.

In an aspect, additive manufacturing device is configured to fabricate the personalized vessel based on the format of the model of the vessel stent. The format of the model of the personalized vessel stent is at least one of STL format and a CAD format.

The above mentioned and other features of the invention will now be addressed with reference to the accompanying drawings. The illustrated embodiments are intended to illustrate but not limit the invention.

BRIEF DESCRIPTION OF THE DRAWINGS

The present invention is further described hereinafter with reference to illustrated embodiments shown in the accompanying drawings, in which.

DETAILED DESCRIPTION

Various embodiments are described with reference to the drawings, wherein like reference numerals are used to refer like elements throughout. In the following description, for the purpose of explanation, numerous specific details are set forth in order to provide thorough understanding of one or more embodiments. It may be evident that such embodiments may be practiced without these specific details.

Figure 1:
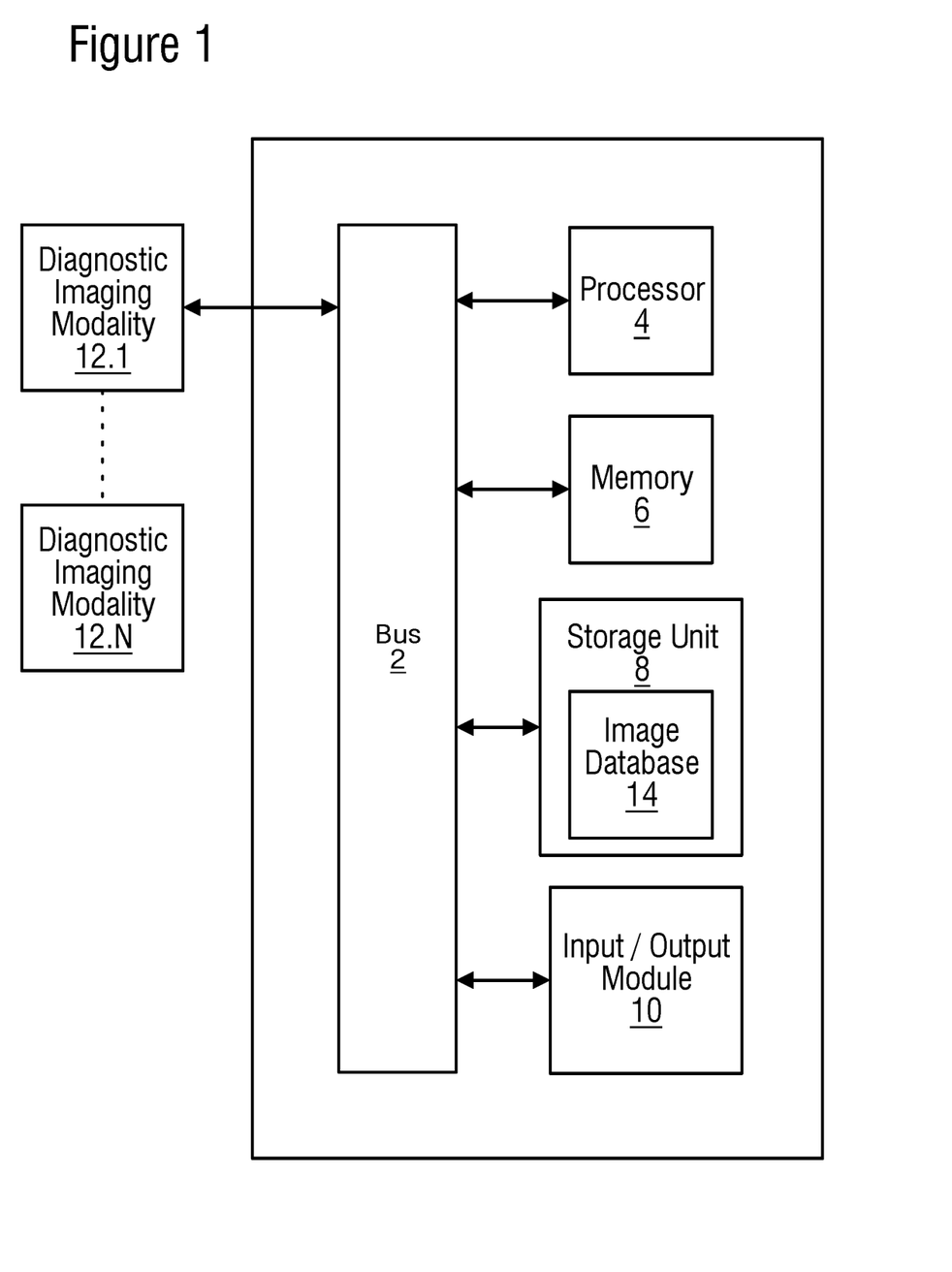
FIG. 1 illustrates an exemplary device for personalizing a vessel stent, in accordance with an embodiment.

FIG. 1 illustrates an exemplary device 1 for personalizing a vessel stent, in accordance with an embodiment. The device 1 includes a communication bus 2, a processor 4, a memory 6, a storage unit 8 and an Input/Output (I/O) module 10. Further, the device 1 is communicatively coupled to a plurality of diagnostic imaging modalities 12.1-12.N. The device 1 is also connected to a database which includes, for example, patient stratification data.

The processor 4, as used herein, means any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. Processor 4 may also include embedded controllers, such as generic or programmable logic devices or arrays, application specific integrated circuits, single-chip computers, and the like.

The memory 6 may be volatile memory and non-volatile memory. The memory 6 may be coupled for communication with processor 4. Processor 4 may execute instructions and/or code stored in memory 6. A variety of computer-readable storage media may be stored in and accessed from memory 6. Memory 6 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In the present embodiment, the memory includes a vessel stent personalization module 15, which is stored in the form of machine-readable instructions on any of the above-mentioned storage media and may be in communication to and executed by processor 4. The vessel stent personalization module 15 further includes modules, which, when executed by the processor 4, results in the personalization of the vessel stent based on the physical and physiological parameters of the subject. The functionalities of the modules are described in greater detail in conjunction with FIG. 2.

The storage unit 8 may be a non-transitory storage medium which stores the images generated by the imaging modalities 12.1-12.N. In an instance, the storage unit 8 stores patient stratification parameters used in the verification of the model of the vessel stent. The storage unit 8 may also include a database of images 14 generated by the plurality of imaging modalities. The communication interface 7 enables the device 1 to communicate with other connected devices via wired or wireless communication protocol known in the art. The input/output unit 10 may include input devices such as keypad, touch-sensitive display, etc. capable of receiving input signal, and output devices such as speaker, printer, display device for outputting, for example, the model of the vessel stent. The communication bus 2 acts as interconnect between processor 4, memory 6, storage unit 8, communication interface 7, and input/output unit 10.

Figure 2:
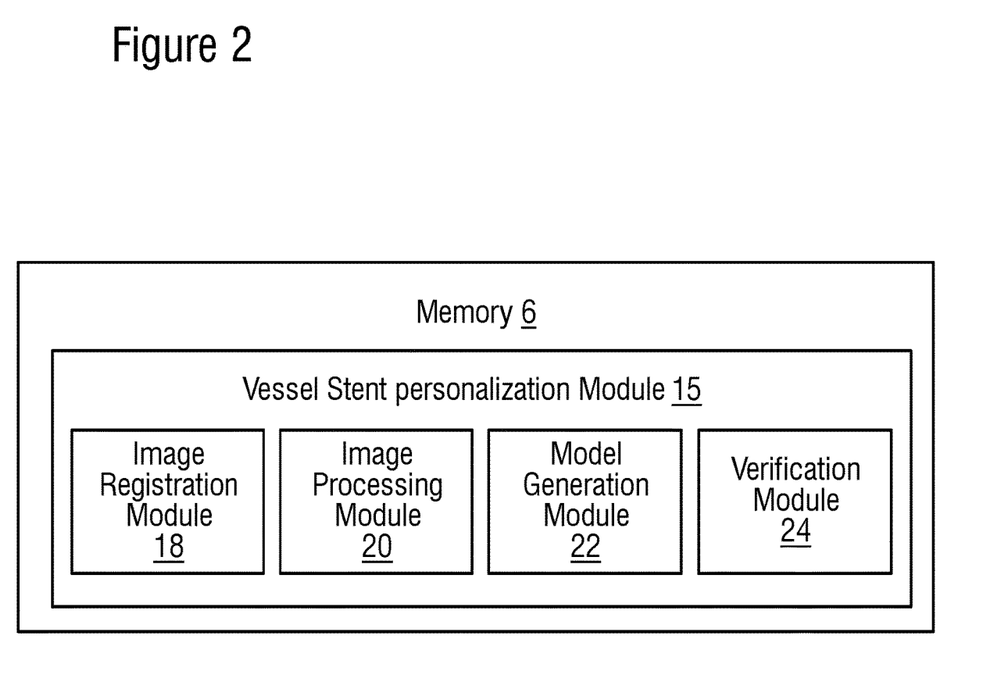
FIG. 2 illustrates an exemplary block diagram of the vessel stent personalization module, in accordance with an embodiment.

FIG. 2 illustrates an exemplary block diagram of the vessel stent personalization module 15, in accordance with an embodiment. The stent personalization module 15 is configured to customize a vessel stent based on various physiological parameters of the subject as well as the region of interest (ROI) in the vessel thereof. The stent personalization module 15 includes an image registration module 18, image processing module 20, model generation module 22, and verification module 24. In an embodiment, the image registration module 18 includes processor executable instructions configured to register images generated by one or more diagnostic imaging modalities. The imaging modalities may include various X-ray based imaging modules, Ultrasound modules, Magnetic Resonance (MR) based modules, Computerized tomography scanning (CT) modules, positron emission tomography (PET) modules. In a preferred embodiment, the images are associated with the cardiac functioning of the subject. The image registration module 18 may register one or more images of the subject in such a manner that the structure of the arteries of the subject is characterized. In some instances, different views of the arteries may be mapped to provide more clarity on the structure of the arteries.

In an embodiment, the image processing module 20 is configured to determine one or more characteristics of the plaque deposited in the ROIs of the arteries. The image processing module 20 determines the nature of plaque, extent of calcification of the plaque, area of stenosis, location of the stenosis and the like. The image processing module 20 is configured to use one or more image processing algorithms to determine the parameters. The image processing algorithms may include segmentation, vesselness detection, vessel centreline detection and the like.

Figure 3:
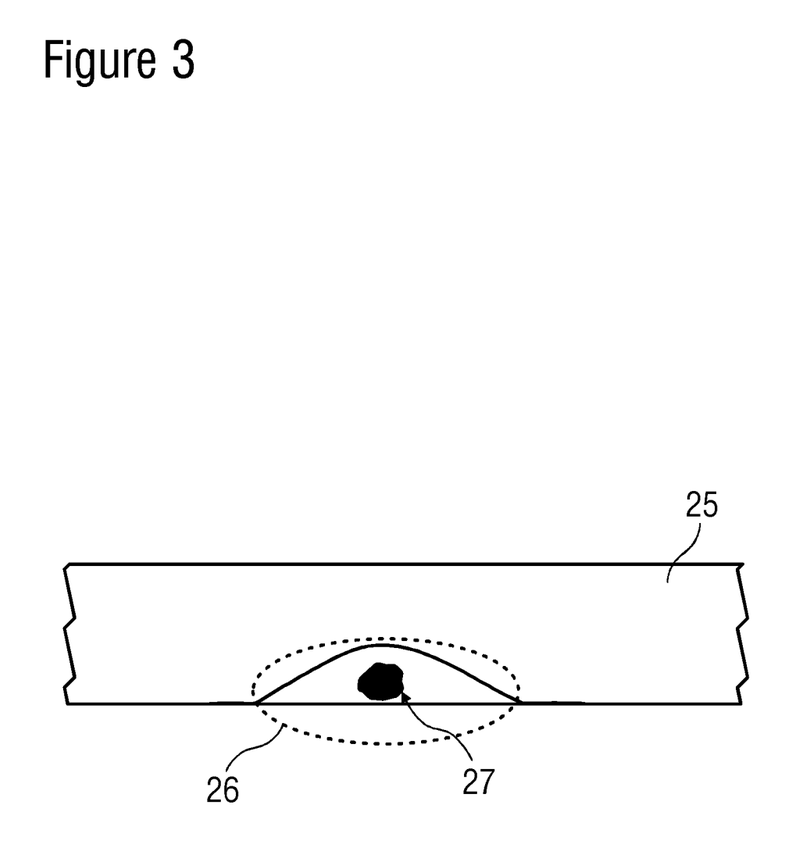
FIG. 3 illustrates an exemplary vessel of a subject with a region of interest, in accordance with an embodiment.

FIG. 3 illustrates an exemplary vessel 25 of the subject depicting a region of interest (ROI) 26. The image processing module 20 may determine that the ROI 26 in the vessel has a calcified region 27 apart from fatty deposits. Further, the image processing module 20 may indicate the length and thickness of the stenosed region 54 and a level of calcification of the calcified region 27 based on the images from different diagnostic imaging modalities. The image processing module 20 finally outputs the parameters associated with the stenosed region of the vessel and the characteristics of the arteries. The image processing module 20 is configured to process images generated by the different imaging modalities as mentioned before.

Figure 4:
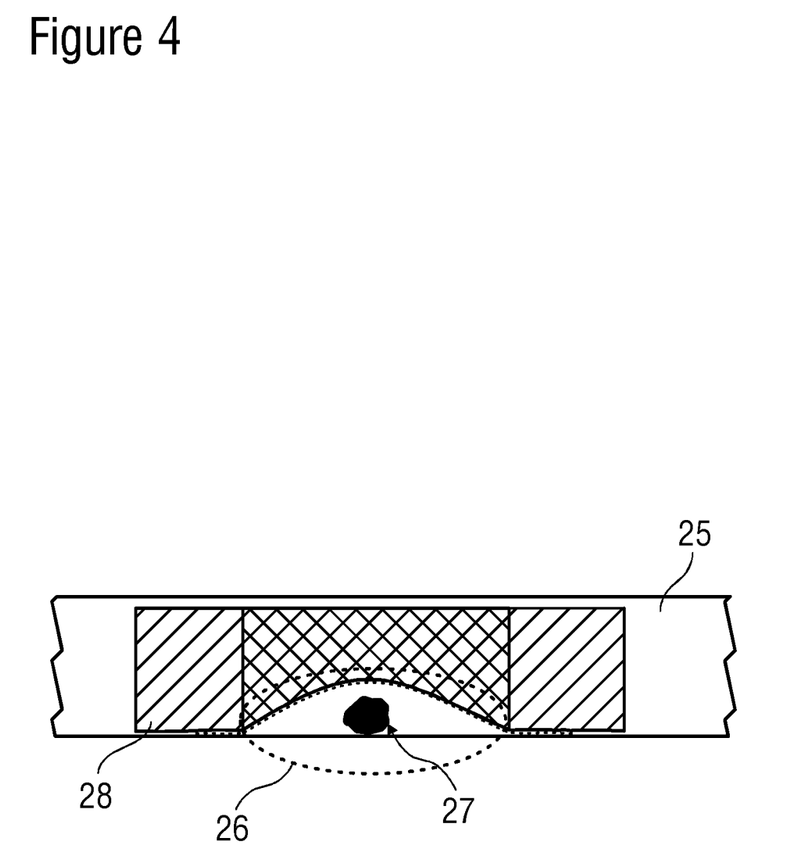
FIG. 4 illustrates an exemplary personalized vessel stent modelled for the subject, in accordance with an embodiment.

In an embodiment, the model generation module 22 generates a personalized multidimensional model of the vessel stent to be used in the subject. FIG. 4 illustrates an exemplary personalized vessel stent 28 modelled for the subject. The model generation module 22 generates a model of the vessel stent 28 personalized for the subject. The model generation module 22 considers the characteristics of the ROI 26 for generating the model of the vessel stent 28. In an exemplary scenario, model generation module 22 is configured to analyze the nature of the ROI 26 and model the vessel stent 28 accordingly. The nature of the ROI may include a soft (uncalcified) region, hard (calcified region) and a mixed type region. For example, model generation module 22 considers that there are calcified region 27 in the vessel 25 and models the vessel stent 28 in a way to exert less pressure over the calcified region 27. It can be seen in FIG. 4 that the model and composition of the personalized vessel stent 28 is such that the vessel stent 28 exerts minimal pressure on the calcified region 27. The contour of the vessel stent 28 may be modelled in a way to avoid the calcified regions 27 of the stenosis. The model generation module 22 may determine a choice of materials, a method of additive manufacturing process to be used, compliance and a burst pressure that is used to inflate a balloon. The model generation module 22 may chose the materials from a group of metallic alloys such as stainless steel, Cobalt alloy, Nickel-Titanium alloy and the like. In an instance, the model generation module 22 may choose a method of additive manufacturing from a group of laser machining, photochemical etching, braiding, knitting and stranding. In another instance, the model generation module 22 may suggest any additions to the vessel stent 28 such as radiopaque coating, drug eluting coating and the like.

In an embodiment, the model generation module 22 may generate a format 60 of the model of the personalized vessel stent 28 for fabrication. The format 60 of the model may be, for example, a STereoLithography (STL) format and a Computer-aided model (CAD) format. The format of the model may be directly used by an additive manufacturing device to fabricate the vessel stent. The model generation module 22 generates the model for the vessel stent based on the parameters such as physical and physiological parameters of the subject and the nature of the plaque deposit.

In an embodiment, the verification module 24 verifies the model of the vessel stent 28 by checking the vessel stent 28 with a model of the cardiovascular system of the subject based on the images generated by the imaging modalities and one or more patient stratification data. The patient stratification data is obtained based on the ethnicity, age and sex of the subject. In an example, the patient stratification data is used to determine a width of the coronary vessel to which the vessel stent is to be administered. The vessel stent is personalized to fit the vessel of the subject based on the patient stratification data. In case the model 60 of the vessel stent 28 does not fit the vessel of the subject derived based on the patient stratification data, the model 60 is changed based on the patient stratification data so that the vessel stent fits the affected vessel of the subject.

Further, the verification module 24 is configured to simulate the inflation of the personalized vessel stent 28 within a model of the coronary vessel of the subject. The simulation may be used for verifying the inflation of the personalized vessel stent under different pressure values of an inflating balloon. Furthermore, the verification module 24 may be used to verify the structure of the fit of the stent with respect to the stenosed region in the vessel. In case the stent design does not appear to fit well in the simulation, the design of the stent may be remodeled for better fit.

Figure 5:
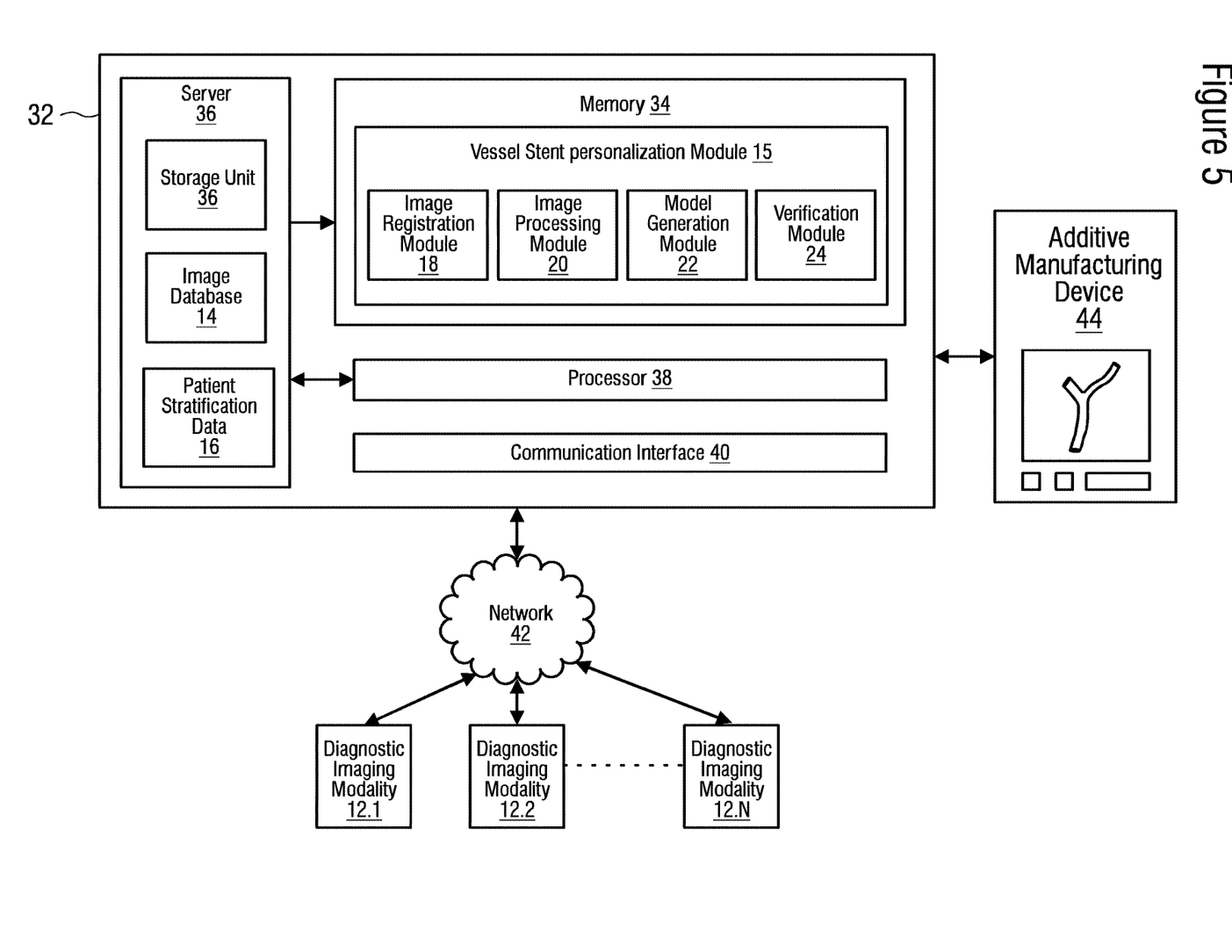
FIG. 5 illustrates an exemplary schematic of a system for personalizing the vessel stent, in accordance with an embodiment.

FIG. 5 illustrates an exemplary schematic of a system 30 for personalizing the vessel stent. The system includes a server 32, an additive manufacturing device 44, a network 42 and imaging modalities 12.1-12.N. The server 32 includes a memory 34, a storage unit 36, a processor 38 and a communication interface 40. The server 32 is connected to the imaging modalities 12.1-12.N via the network 42. The network 42 may be a wired or a wireless network known in the art. The memory 34 includes the vessel stent personalization module in the form of processor executable instructions, as explained in FIG. 2. The storage 36 includes, for example, a database 14 of images generated by the imaging modalities 12.1-12.N and patient stratification data. The processor 38 is configured to execute the instructions stored in the memory 34. Further, the server 32 communicates with the imaging modalities 12.1-12.N using the network 42 through the communication interface 40. The communication interface 40 may be a network interface card. Additionally, the server 32 is communicatively coupled to an additive manufacturing device 44. The additive manufacturing device 44 may be capable of fabricating personalized vessel stents based on the format of the model of the vessel stent output by the server 32. The additive manufacturing device 44 is equipped to fabricate the personalized vessel stent using additive manufacturing methods such as, sintering, laser etching, vapour deposition, braiding, meshing and the like.

Figure 6:
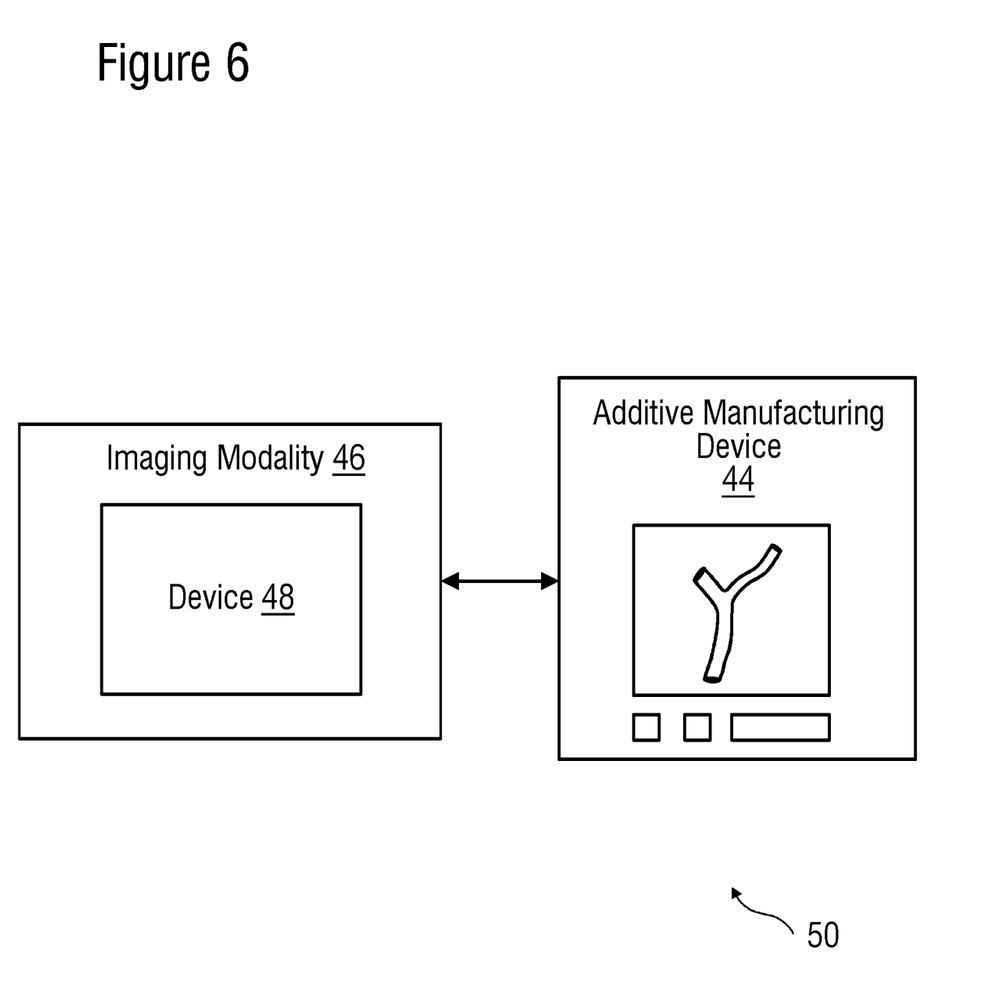
FIG. 6 illustrates an exemplary block diagram of the device for personalizing the vessel stent, in accordance with an embodiment.

FIG. 6 illustrates an exemplary block diagram 50 of an apparatus for personalizing the vessel stent, in accordance with an embodiment. The apparatus includes an imaging modality 46, device 48 and an additive manufacturing device 44. The device 48 is communicatively coupled to the imaging modality 46 thereby making the imaging modality 46 capable of personalizing vessel stents. In an embodiment, the imaging modality 46 may include the hardware of the device 48 as an integral part of the hardware thereof. The imaging modality 46 may include the necessary input/output devices for displaying and customizing the vessel stent. The imaging modality may include, for example, a keyboard, a mouse and a display. The additive manufacturing device 44 is communicatively coupled to the imaging modality 46 such that the model of the personalized vessel stent can be directly communicated to the additive manufacturing device 44 for fabrication. In FIG. 4, the additive manufacturing device 44 may be replaced by any other device which can make use of the model of the vessel stent.

Figure 7:
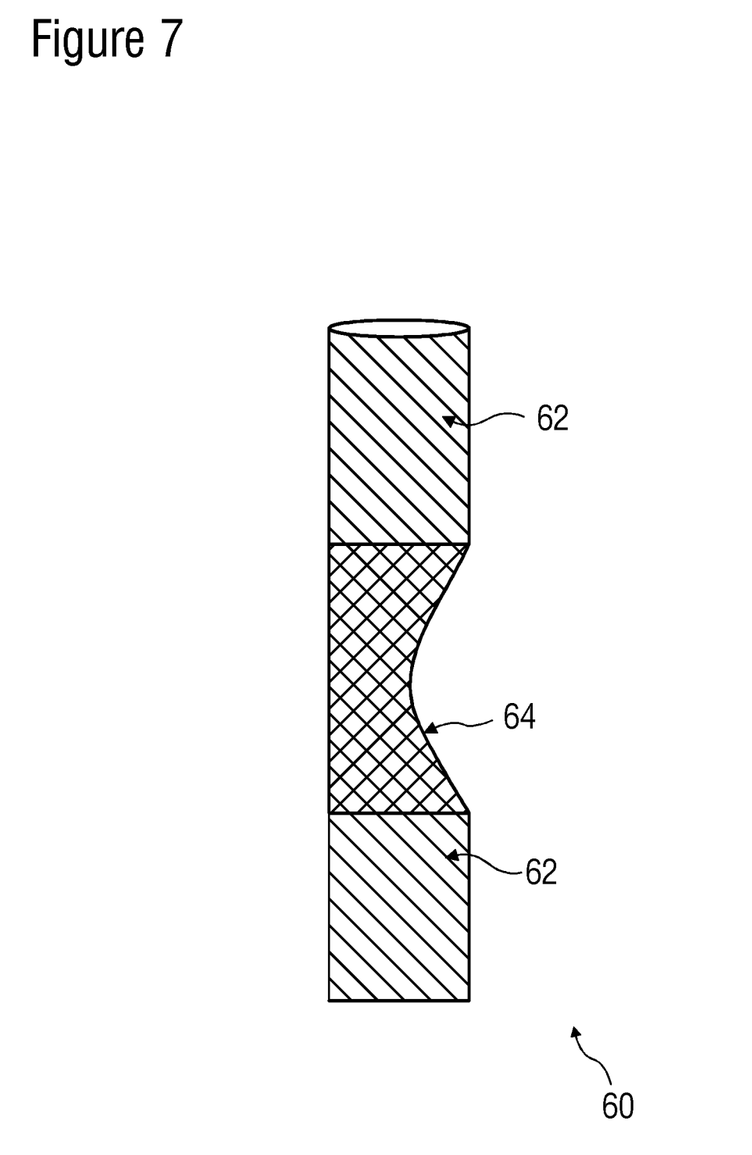
FIG. 7 illustrates an exemplary vessel stent fabricated using the aforementioned system, in accordance with an embodiment.

FIG. 7 illustrates an exemplary vessel stent 60 fabricated using the system 1, in accordance with an embodiment. The vessel stent 60 may be fabricated based on the format of the model of the vessel stent generated by system 1. As shown in FIG. 7, the vessel stent 60 is composed of two different materials 62 and 64. In an exemplary embodiment, the materials may include any material which is biocompatible and can be used in additive manufacturing. Some examples of the materials include Tin based alloy, stainless steel, Cobalt based alloy, and Aluminium based alloy. In another exemplary embodiment, the materials may include plastics such as polyvinyl and polycarbonate. The materials are selected by the model generation module 22 based on the parameters associated with the stenosed region. The parameters may include, for example, nature and composition of the stenosed region and calcification of the stenosed region.

Figure 8:
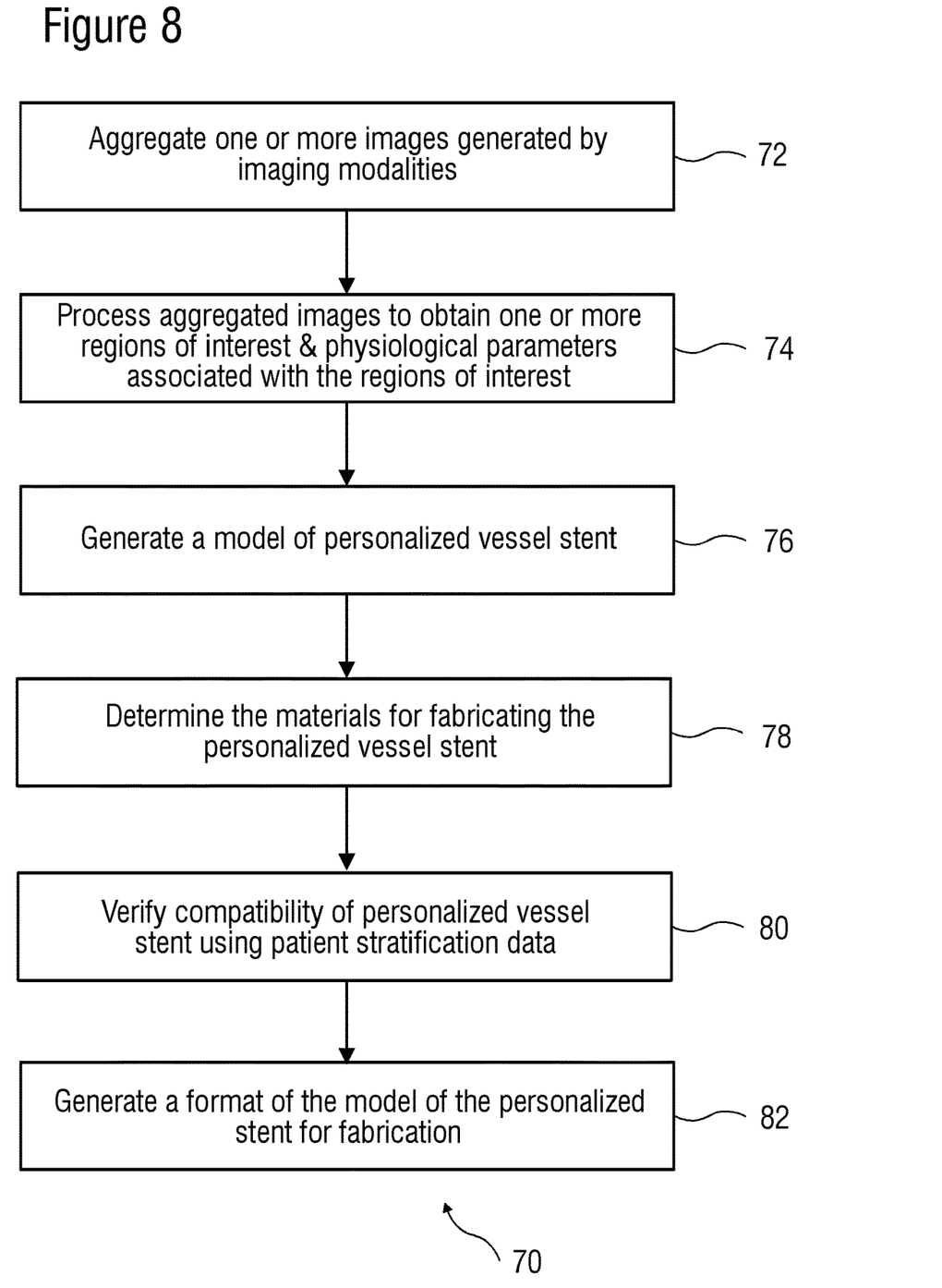
FIG. 8 illustrates a block diagram of exemplary method steps for personalizing the vessel stent, in accordance with an embodiment.

FIG. 8 illustrates a block diagram 70 of exemplary method steps for personalizing the vessel stent, in accordance with an embodiment. In step 72, one or more images generated by one or more imaging modalities are aggregated by a processor. The images are generated by one or more diagnostic imaging modalities. In an example, an angiography, CT scan and MRI scan of the cardiovascular structure of the subject may be aggregated from the respective imaging modalities. At step 74, the aggregated images are processed to obtain one or more regions of interest and one or more physiological parameters associated with one or more region of interest (ROI). In the example, the ROI may be a stenosed region in the cardiac vessel of the subject. The stenosed region may include plaque deposits, occasionally having calcified regions therein. The ROIs may be determined by applying image processing algorithms on a combination of the aggregated images. At step 76, a model of the personalized vessel stent based on the one or more parameters associated with the region of interest and one or more physiological parameters associated with the subject is generated. The model of the personalized vessel stent may be based on the nature and extent of calcification of the ROI. Further, the personalized vessel stent may be based on the physiological parameters of the subject. Further, the width and thickness of the blood vessel of the subject may be determined at step 74, which may also factor in the generation of the vessel stent.

At step 78, materials for fabricating the personalized vessel stent are determined based on the one or more parameters associated with the ROI. Referring to the example, the material of the personalized vessel stent may be determined based on, for example, the composition of the stenosed area and the extent of calcification of stenosed area. In case there is a calcification in the stenosed area, then the composition of the vessel stent is modified so that the stent does not exert pressure on the stenosed area, which may lead to bursting of the blood vessel. At step 80, the compatibility of the personalized vessel stent may be verified using patient stratification data. Parameters, such as diameter of coronary vessel, may be obtained by patient stratification data. Physiological data of the patient such as weight, age, sex and ethnicity may be used to retrieve the appropriate parameters required for verification of the model of the vessel stent. In case the model of the vessel stent does not match based on the patient stratification data, the model of the vessel stent is remodeled. Further, the revised model is tested, and the model that passes the test is communicated for fabrication. At step 82, a format of the model of the personalized vessel stent is generated for fabrication. The format may be communicated to the additive manufacturing device for fabrication. The format may be accompanied with the type of additive manufacturing process to be used and the materials to be used for fabricating the personalized vessel stent.

The method and system described herein allows physicians to fabricate personalized stents in real-time using physiological parameters of the subject. The method and system takes into account the calcification in the stenosed region for modelling the vessel stent. As a result, the vessel stent is safe for the subject. The method and system utilizes images from a plurality of imaging modalities for modelling the vessel stent that leads to efficient modelling of the vessel stent. The vessel stent is modelled so as to exert minimal stress on the calcified region of the ROI. Using the method and system described, it is possible to fabricate the stent with different materials based on the location of the calcified region in the ROI. The method and system enables the model of personalized vessel stents for treatment of vascular obstructions in any part of the body.

While the present invention has been described in detail with reference to certain embodiments, it should be appreciated that the present invention is not limited to those embodiments. In view of the present disclosure, many modifications and variations would be present themselves, to those skilled in the art without departing from the scope of the various embodiments of the present invention, as described herein. The scope of the present invention is, therefore, indicated by the following claims rather than by the foregoing description. All changes, modifications, and variations coming within the meaning and range of equivalency of the claims are to be considered within their scope.

We claim:

1. A method for customizing a vessel stent for a subject, the method comprising:
aggregating, by a processor, one or more images generated by one or more imaging modalities;

processing, by the processor, the one or more images to obtain one or more regions of interest (ROIs) and one or more parameters characterising the ROIs in a vessel of the subject;

generating, by the processor, a computer model of the personalized vessel stent, the computer model generated from the one or more parameters characterizing the ROIs and physiological parameters of the subject, the computer model representing the personalized vessel stent and including a contour of the personalized stent different than the vessel;

determining, by the processor, one or more materials for fabricating the personalized vessel stent based on the one or more parameters associated with the region of interest; and generating, by the processor, a format of the model of the personalized vessel stent for fabrication.

2. The method of claim 1 further comprising, verifying the computer model of the personalized vessel stent from the one or more physiological parameters characterizing the one or more ROIs and one or more patient stratification parameters.

3. The method of claim 1, wherein patient stratification parameters are determined based on a physical parameter and the physiological parameters of the subject.

4. The method of claim 1, wherein the one or more ROIs comprise a stenosed region in the vessel.

5. The method of claim 1, wherein the parameters characterizing the one or more ROIs include a length, a thickness, a composition, a level of calcification, and a distribution of a plaque deposition at the stenosed region.

6. The method of claim 1, wherein the one or more materials for fabricating the personalized vessel stent are determined based on the parameters associated with the ROIs.

7. The method of claim 1, wherein the one or more materials used in the fabrication of personalized vessel stent comprise any material that is biocompatible and is useable in an additive manufacturing process.

8. The method of claim 1, wherein the personalized vessel stent is fabricated by an additive manufacturing process.

9. A device for customizing a vessel stent for a subject, the device comprising:
a processor coupled to one or more diagnostic imaging modalities;
a memory coupled with the processor, wherein the memory comprises processor-executable instructions in the form of vessel stent personalization module configured to:
aggregate one or more images generated by one or more imaging modalities;
process the one or more images to obtain one or more regions of interest and one or more physiological parameters associated with one or more region of interest (ROI);
generate a computer model representing the personalized vessel stent, the computer model generated from the one or more parameters characterizing the ROIs and one or more patient stratification parameters, the computer model representing the personalized vessel stent with a contour different than the vessel;
determine one or more materials for fabricating the personalized vessel stent based on the one or more parameters associated with the ROIs; and
generate a format of the model of the personalized vessel stent for fabrication.

10. The device of claim 9, wherein the processor is configured to verify the computer model of the personalized vessel stent based on the one or more parameters associated with the one or more ROI and one or more of the patient stratification parameters.

11. The device of claim 9, wherein the processor is communicatively coupled with an additive manufacturing device to fabricate the personalized vessel stent.

12. The device of claim 9, wherein the diagnostic imaging modality is at least one of an X-ray imaging modality, a computed tomography (CT) imaging modality and a magnetic resonance imaging (MRI) modality.

13. A system for personalizing a vessel stent for a patient, the system comprising:
one or more diagnostic imaging modalities,
a processor,
a memory associated with the processor comprising executable instructions configured for:
aggregate one or more images generated by one or more imaging modalities, the one or more images representing a vessel of the patient;
process the said one or more images to obtain one or more regions of interest (ROIs) of the vessel and one or more physiological parameters associated with the one or more ROIs;
generate a model of the personalized vessel stent based on the one or more parameters associated with the ROIs and one or more patient stratification parameters, the model representing the personalized vessel stent with a contour different than the vessel;
determine one or more materials for fabricating the personalized vessel stent based on the one or more physiological parameters associated with the ROIs; and
generate a format of the model of the personalized vessel stent for fabrication; and
an additive manufacturing device configured to fabricate the personalized vessel stent using the format of the model.

14. The system of claim 13, the processor is configured to verify a compatibility of the model of the personalized vessel stent by using one or more of the patient stratification parameters based on a physical parameter and the physiological parameters of the subject.

15. The system of claim 13, wherein the additive manufacturing device is configured to fabricate the personalized vessel stent using one or more materials.

16. The system of claim 13, wherein the format of the model of the personalized vessel stent is at least one of STereoLithography (STL) format and a Computer Aided Model (CAD) format.

* * * * *